United States Patent
DeShazo et al.

(10) Patent No.: US 11,464,981 B2
(45) Date of Patent: Oct. 11, 2022

(54) SYSTEMS AND METHODS FOR OUTPUT CHANNEL ARCHITECTURES IN IMPLANTABLE PULSE GENERATORS

(71) Applicant: ADVANCED NEUROMODULATION SYSTEMS, INC., Plano, TX (US)

(72) Inventors: Daran DeShazo, Lewisville, TX (US); Steven Boor, Plano, TX (US); Gavin L. Rade, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 358 days.

(21) Appl. No.: 16/397,875

(22) Filed: Apr. 29, 2019

(65) Prior Publication Data
US 2020/0338352 A1 Oct. 29, 2020

(51) Int. Cl.
*A61N 1/36* (2006.01)
*A61N 1/378* (2006.01)
*A61N 1/05* (2006.01)

(52) U.S. Cl.
CPC ....... *A61N 1/36157* (2013.01); *A61N 1/0534* (2013.01); *A61N 1/0551* (2013.01); *A61N 1/36125* (2013.01); *A61N 1/36142* (2013.01); *A61N 1/36164* (2013.01); *A61N 1/378* (2013.01)

(58) Field of Classification Search
CPC ........................ A61N 1/36157; A61N 1/36125
See application file for complete search history.

(56) References Cited

U.S. PATENT DOCUMENTS

| | | | |
|---|---|---|---|
| 6,181,969 B1 * | 1/2001 | Gord | A61N 1/32 607/57 |
| 7,212,110 B1 | 5/2007 | Martin et al. | |
| 7,228,179 B2 | 6/2007 | Campen et al. | |
| 7,571,007 B2 | 8/2009 | Erickson et al. | |

(Continued)

FOREIGN PATENT DOCUMENTS

WO    2001093953 A1    12/2001

OTHER PUBLICATIONS

International Search Report and Written Opinion for International Patent Application No. PCT/US2020/021810, dated Jun. 10, 2020, 15 pages.

*Primary Examiner* — Eric D. Bertram
(74) *Attorney, Agent, or Firm* — Norton Rose Fulbright US LLP

(57) ABSTRACT

The present disclosure provides systems and methods for an output architecture for an implantable pulse generator of a neurostimulation system. The output architecture includes a power supply, a plurality of outputs, a global source current regulator coupled to the power supply and operable to source current from the power supply to the plurality of outputs through a plurality of source current branches, a global sink current regulator operable to sink current from the plurality of outputs to ground through a plurality of sink current branches, a current source branch selector operable to select, for each of the plurality of outputs, an amount of current sourced from the plurality of source current branches, and a current sink branch selector operable to select, for each of the plurality of outputs, an amount of current sunk to the plurality of sink current branches.

20 Claims, 4 Drawing Sheets

(56) References Cited

U.S. PATENT DOCUMENTS

| | | | |
|---|---|---|---|
| 8,738,135 B1* | 5/2014 | Lee | A61N 1/3752 |
| | | | 607/37 |
| 9,056,206 B2* | 6/2015 | Torgerson | A61N 1/36082 |
| 2005/0267546 A1* | 12/2005 | Parramon | A61N 1/025 |
| | | | 607/48 |
| 2006/0170486 A1 | 8/2006 | Tranchina et al. | |
| 2007/0038250 A1* | 2/2007 | He | A61N 1/36185 |
| | | | 607/2 |
| 2007/0100399 A1* | 5/2007 | Parramon | A61N 1/0551 |
| | | | 607/68 |
| 2010/0125315 A1* | 5/2010 | Parramon | A61N 1/36157 |
| | | | 607/59 |
| 2011/0093041 A1* | 4/2011 | Straka | A61N 1/36125 |
| | | | 607/59 |
| 2011/0276103 A1* | 11/2011 | Maile | A61N 1/36125 |
| | | | 607/9 |
| 2012/0071950 A1* | 3/2012 | Archer | A61N 1/36125 |
| | | | 607/66 |
| 2018/0071516 A1* | 3/2018 | Weiss | A61N 1/0551 |
| 2018/0071520 A1* | 3/2018 | Weerakoon | A61N 1/36062 |
| 2019/0083796 A1* | 3/2019 | Weerakoon | A61N 1/36125 |

\* cited by examiner

SYSTEMS AND METHODS FOR OUTPUT CHANNEL ARCHITECTURES IN IMPLANTABLE PULSE GENERATORS

FIELD OF THE DISCLOSURE

The present disclosure relates generally to neurostimulation systems, and more particularly to output channel architectures for implantable pulse generators.

BACKGROUND ART

Neurostimulation is an established neuromodulation therapy for the treatment of movement disorders. For example, neurostimulation has been shown to improve cardinal motor symptoms of Parkinson's Disease (PD), such as bradykinesia, rigidity, and tremors. Types of neurostimulation include deep brain stimulation (DBS) and spinal cord stimulation (SCS).

In both SCS and DBS, for stimulation purposes, it may be desirable to create one or more virtual electrodes at locations between the physical electrodes in the system. For example, lead migration in SCS and lead placement in DBS may result in physical electrodes being positioned at a location other than a desired stimulation location for precise electric field shaping. Accordingly, one or more virtual electrodes may be created by applying controlled stimulation at a plurality of physical electrodes simultaneously. That is, the controlled stimulation at a plurality of physical electrodes may be used to effectively simulate stimulation being applied by a non-existent electrode (i.e., the virtual electrode).

In at least some known systems, virtual electrodes are created using either i) interleaved stimulation pulses generated using low-overhead current regulators, or ii) simultaneous stimulation pulses generated using current mirror devices. However, known systems are generally not capable of creating virtual electrodes using both time-multiplexed and simultaneous current delivery using low-overhead current regulators.

Further, at least some existing implantable pulse generators (IPGs) include a passive discharge current path that facilitates discharging selected (i.e., active) electrodes. However, these IPGs generally have no ability to monitor or discharge other (i.e., non-active) electrodes. Further, for patient safety and electrode reliability, it is important to manage potentials that build up across direct current (DC) blocking caps in the IPG, and across electrode/tissue interfaces. For example, it is desirable for patient safety and electrode integrity reasons to maintain these potentials below a predetermined threshold. Further, unmanaged charge build-up may also negatively impact stimulation efficiency and impedance measurement accuracy.

BRIEF SUMMARY OF THE DISCLOSURE

In one embodiment, the present disclosure is directed to an output architecture for an implantable pulse generator of a neurostimulation system. The output architecture includes a power supply, a plurality of outputs, a global source current regulator coupled to the power supply and operable to source current from the power supply to the plurality of outputs through a plurality of source current branches, a global sink current regulator operable to sink current from the plurality of outputs to ground through a plurality of sink current branches, a current source branch selector operable to select, for each of the plurality of outputs, an amount of current sourced from the plurality of source current branches, and a current sink branch selector operable to select, for each of the plurality of outputs, an amount of current sunk to the plurality of sink current branches.

In another embodiment, the present disclosure is directed to a neurostimulation system. The neurostimulation system includes a stimulation lead comprising a plurality of electrodes and an implantable pulse generator communicatively coupled to the stimulation lead. The implantable pulse generator includes an output architecture that includes a power supply, a plurality of outputs, a global source current regulator coupled to the power supply and operable to source current from the power supply to the plurality of outputs through a plurality of source current branches, a global sink current regulator operable to sink current from the plurality of outputs to ground through a plurality of sink current branches, a current source branch selector operable to select, for each of the plurality of outputs, an amount of current sourced from the plurality of source current branches, and a current sink branch selector operable to select, for each of the plurality of outputs, an amount of current sunk to the plurality of sink current branches.

In another embodiment, the present disclosure is directed to a method of assembling an output architecture for an implantable pulse generator. The method includes coupling a global source current regulator between a power supply and a plurality of outputs, the global source current regulator operable to source current from the power supply to the plurality of outputs through a plurality of source current branches, coupling a global sink current regulator to the plurality of outputs, the global sink current regulator operable to sink current from the plurality of outputs to ground through a plurality of sink current branches, coupling a current source branch selector between the global source current regulator and the plurality of outputs, the current source branch selector operable to select, for each of the plurality of outputs, an amount of current sourced from the plurality of source current branches, and coupling a current sink branch selector between the global sink current regulator and the plurality of outputs, the current sink branch selector operable to select, for each of the plurality of outputs, an amount of current sunk to the plurality of sink current branches.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for an output architecture for an implantable pulse generator. The output architecture includes a power supply and a plurality of outputs. A global source current regulator is operable to source current from the power supply to the plurality of outputs through a plurality of source current branches, and a global sink current regulator is operable to sink current from the plurality of outputs to ground through a plurality of sink current branches. Further, a current source branch selector is operable to select an amount of current sourced from the plurality of source current branches, and a current sink branch selector is operable to select an amount of current sunk to the plurality of sink current branches.

Neurostimulation systems are devices that generate electrical pulses and deliver the pulses to nerve tissue of a patient to treat a variety of disorders. One category of neurostimulation systems is deep brain stimulation (DBS). In DBS, pulses of electrical current are delivered to parts of a subject's brain, for example, for the treatment of movement and effective disorders such as PD and essential tremor. Another category of neurostimulation systems is spinal cord stimulation (SCS).

Neurostimulation systems generally include a pulse generator and one or more leads. A stimulation lead includes a lead body of insulative material that encloses wire conductors. The distal end of the stimulation lead includes multiple electrodes, or contacts, that are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted within a subcutaneous pocket created during the implantation procedure.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead.

Figure 1:
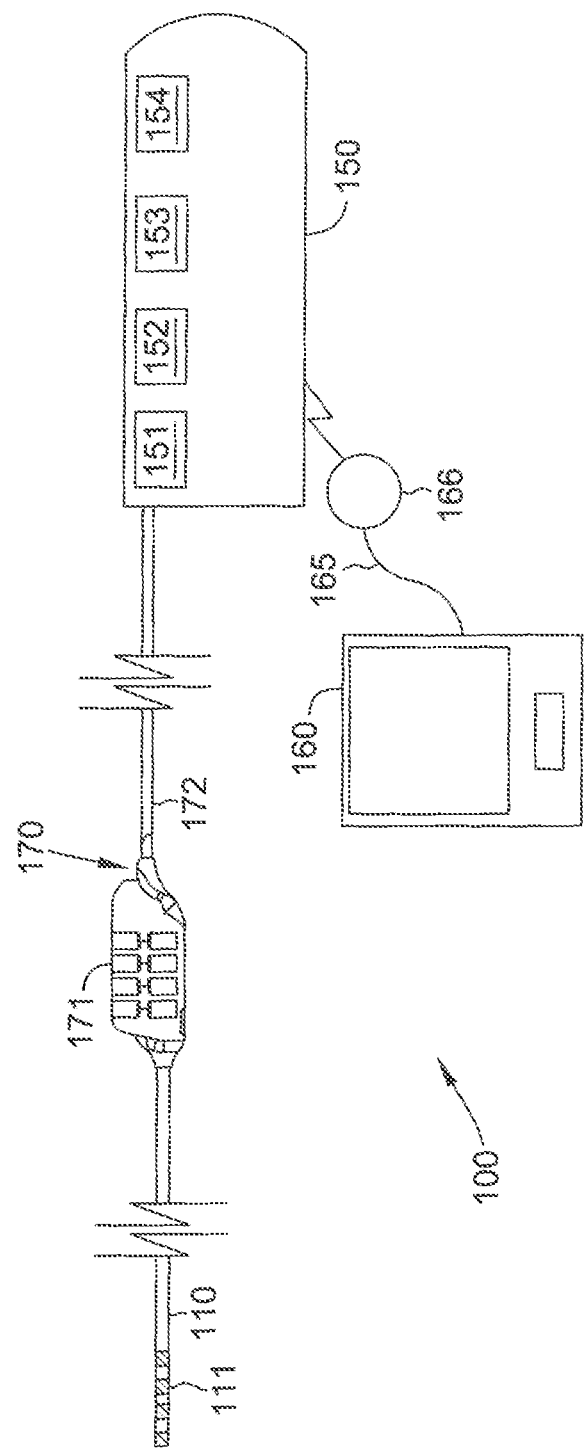
FIG. 1 is a schematic view of one embodiment of a stimulation system.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. Alternatively, system 100 may include an external pulse generator (EPG) positioned outside the patient's body. IPG 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may comprise one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally, or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced by a magnetic field in the secondary coil. The current induced in the coil of the implantable pulse generator is rectified and regulated to recharge the battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. In the methods and systems described herein, parameters may include, for example, a number of pulses in a burst (e.g., 3, 4, or 5 pulses per burst), an intra-burst frequency (e.g., 500 Hz), an inter-burst frequency (e.g., 40 Hz), and a delay between the pulses in a burst (e.g., less than 1 millisecond (ms)).

IPG 150 modifies its internal parameters in response to the control signals from controller device 160 to vary the stimulation characteristics of stimulation pulses transmitted through stimulation lead 110 to the tissue of the patient.

Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

The systems and methods described herein provide an IPG output architecture that provides several advantages over at least some known existing neurostimulation systems. For example, the IPG output architecture described herein enables low-overhead fractionalized constant current to be sourced from a positive power supply (VANODE). This enables efficient virtual electrode creation during anodic stimulation. Further, the IPG output architecture described herein enables low-overhead fractionalized constant current to be sunk to a negative power supply (e.g., ground). This enables efficient virtual electrode creation during cathodic stimulation.

In addition, the IPG output architecture described herein includes a low-impedance connection to a reference voltage (VREF) as a stimulation reference. This connection may be connected to the positive power supply for cathodic stimulation or to ground for anodic stimulation. It is also possible to connect the reference voltage to intermediate voltages for enhanced immunity to external interference (e.g., from magnetic resonance imaging (MRI) devices or theft-detection devices). The IPG output architecture described herein may also include connections to background discharge nodes (DIS1 and DIS2) for managing background discharge.

The benefits provided by the IPG output architecture described herein include efficient creation of virtual electrodes for both anodic and cathodic stimulation, as well as flexible and effective management of discharging of non-active electrodes. Because only the stimulation current is sourced from the positive voltage source (which can be a multiple of a battery voltage), these benefits are realized efficiently with relatively minimal battery current draw. Other benefits provided by the IPG output architecture descried herein include the ability to simultaneously control currents at the positive voltage source and ground to reduce stimulation interference during exposure to MRI fields or other similar EMI fields.

Figure 2A:
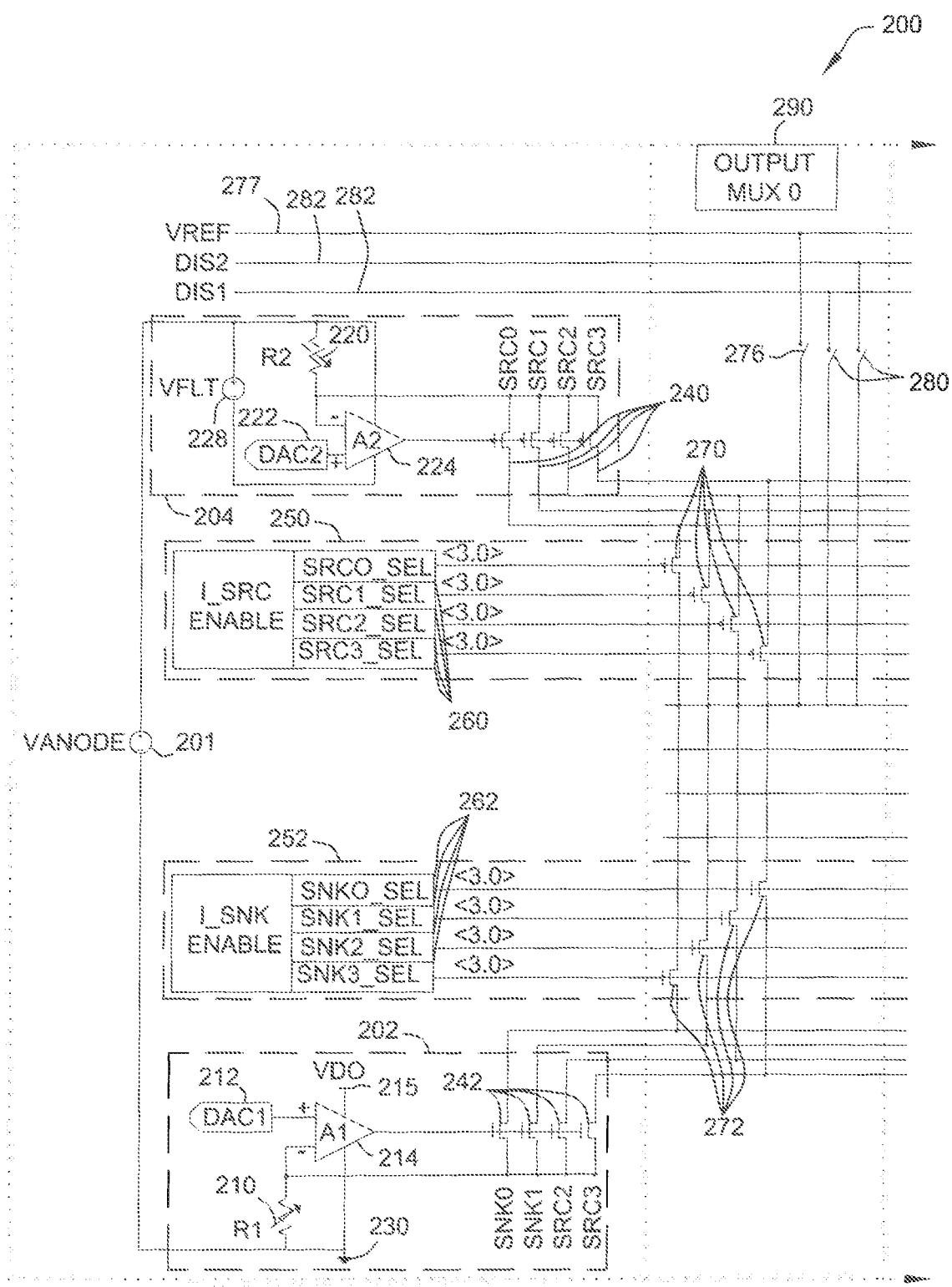
FIGS. 2A and 2B is a circuit diagram of one embodiment of an output architecture that may be used with the stimulation system shown in FIG. 1.
Figure 2B:
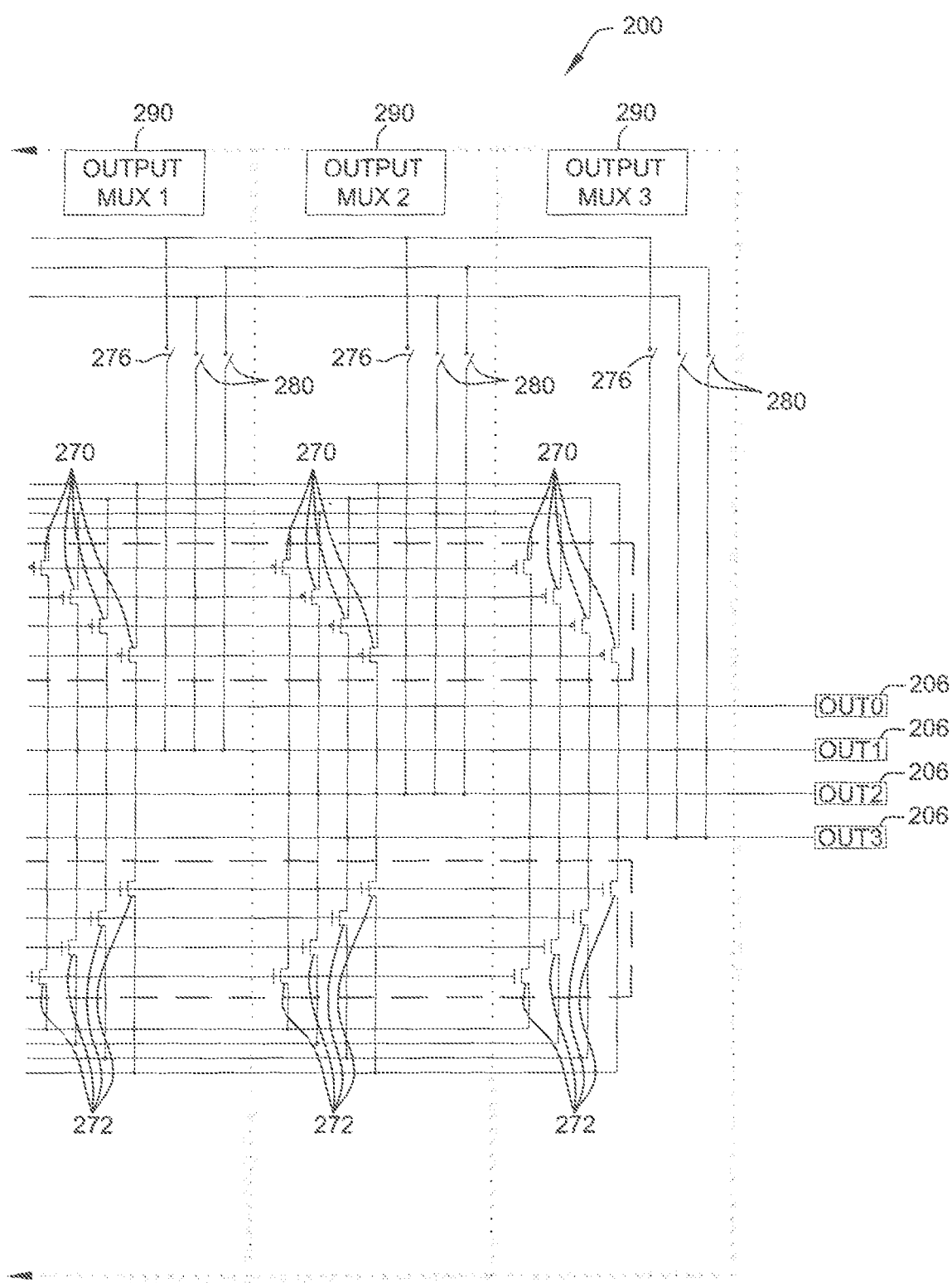

FIGS. 2A and 2B are a circuit diagram of one embodiment of an IPG output architecture 200 that may be used with stimulation system 100 (shown in FIG. 1). For example, pulse generating circuitry 152 (shown in FIG. 1) may be implemented using output architecture 200.

As shown in FIGS. 2A and 2B, output architecture 200 includes a positive power supply 201 (VANODE), a global sink current regulator 202, and a global source current regulator 204. Positive power supply 201 is coupled between global sink current regulator 202 and global source current regulator 204. Further, output architecture 200 includes a plurality of outputs 206 (OUT0, OUT1, OUT2, and OUT3). In this embodiment, output architecture 200 includes four outputs 206. Alternatively, output architecture 200 may include any suitable number of outputs.

In this embodiment, global sink current regulator 202 includes a first programmable resistor 210 (R1), a first voltage digital to analog converter 212 (DAC1), and a first amplifier 214 (A1) that is configured as a voltage-to-current converter. Further, global source current regulator 204 includes a second programmable resistor 220 (R2), a second voltage digital to analog converter 222 (DAC2), and a second amplifier 224 (A2) that is configured as a voltage-to-current converter.

Global source current regulator 204 enables low-overhead fractionalized constant current to be sourced from positive power supply 201. This enables efficient virtual electrode creation during anodic stimulation. Specifically, global source current regulator 204 sets a total amount of current sourced from positive power supply 201 to outputs 206. Four source current branches 240 output current from global source current regulator 204 in this embodiment. Alternatively, global source currently regulator may include any suitable number of source current branches 240.

In this embodiment, first amplifier 214 is powered by using a positive supply voltage 215 (VDD). Further, in this embodiment, second amplifier 224 is powered by a floating capacitive charge pump 228 (VFLT). This avoids powering second amplifier 224 using positive power supply 201, which may incur a battery current penalty (i.e., reducing the total amount of current that will be sourced from positive power supply 201).

Global sink current regulator 202 enables low-overhead fractionalized constant current to be sunk to a negative power supply (e.g., ground 230). This enables efficient virtual electrode creation during cathodic stimulation. Specifically, global sink current regulator 202 sets a total amount of current sunk from outputs 206 to ground 230. Four sink current branches 242 input current to global sink current regulator 202 in this embodiment. Alternatively, global sink current regulator 202 may include any suitable number of sink current branches 242.

In this embodiment, output architecture 200 further includes a current source branch selector 250 and a current sink branch selector 252. Current source branch selector 250 selects, for each output 206, the fraction of the total current to be sourced from source current branches 240. Current source branch selector 250 accomplishes this using a plurality of source decoders 260 (SRC0_SEL, SCR1_SEL, SRC2_SEL, and SRC3_SEL). Each source decoder 260 is associated with one source current branch 240. Further, each source decoder 260 controls a plurality of source selection switches 270 to ensure that current from the associated source current branch 240 is only sourced to one output 206. In some scenarios, all source current branches 240 may source current to the same output 206.

Similarly, current sink branch selector 252 selects, for each output 206, the fraction of the total current to be sunk into sink current branches 242. Current sink branch selector 252 accomplishes this using a plurality of sink decoders 262 (SNK0_SEL, SNK1_SEL, SNK2_SEL, and SNK3_SEL). Each sink decoder 262 is associated with one sink current branch 242. Further, each sink decoder 262 controls a plurality of sink selection switches 272 to ensure that current to the associated sink current branch 242 is only sunk from one output 206. In some scenarios, all sink current branches 242 may sink current from the same output 206. In this embodiment, current source branch selector 250 and current sink branch selector 252 are controlled and/or implemented using controller 151.

In this embodiment, as shown in FIGS. 2A and 2B, output architecture 200 further includes a plurality of low-impedance reference voltage switches 276. Reference voltage switches 276 enable selectively connecting outputs 206 to a selectable reference voltage 277 (VREF).

Further, output architecture 200 includes a plurality of resistive discharge switches 280 in this embodiment. Discharge switches 280 enable selectively connecting outputs 206 to discharge rails 282 (DIS1 and DIS2) for background discharge and monitoring capability. This allows output architecture 200 to passively discharge non-active electrodes. In this embodiment, output architecture 200 includes two discharge rails 282. Alternatively, output architecture 200 may include any suitable number of discharge rails 282.

Reference voltage 277 may be applied to an output 206 when electric field shaping is not needed around one type of stimulation electrode—i.e., either the anode or the cathode. Reference voltage 277 may also be used for applying a common-mode voltage to patient tissue, which may be beneficial in reducing stimulation interference from MRI/EMI.

Discharge rails 282 may be useful for maintaining electrodes not being used for stimulation in a charge neutral state. This may be applicable to alleviate electrode integrity degradation which might otherwise be caused by low-level leakages in the neurostimulator circuitry, or if residual charge remains on an electrode after prior therapy delivery.

Discharge rails 282 may also be useful for the use of electrodes as Kelvin connections in the diagnostic monitoring of lead integrity and/or electrode charge-state monitoring.

In this embodiment, the switching circuitry for each output 206 is implemented in a corresponding multiplexer 290 (Output MUX 0, Output MUX 1, Output MUX 2, and OUTPUT MUX 3). That is, each multiplexer 290 includes source selection switches 270, sink selection switches 272, reference voltage switches 276, and discharge switches 280 for the associated output 206. Alternatively, any suitable switching architecture may be used.

Output architecture 200 enables flexible and efficient shaping of a stimulation electric field for neurostimulation systems. For example, output architecture 200 provides both time-multiplexed and simultaneous current delivery using low-overhead current regulators for flexible and efficient virtual electrode creation. Further, output architecture 200 allows for passively discharging non-active electrodes as described herein. Specifically, discharge switches 280 enable discharging and/or monitoring of non-active electrodes, enhancing management of electrode potentials.

Figure 3:
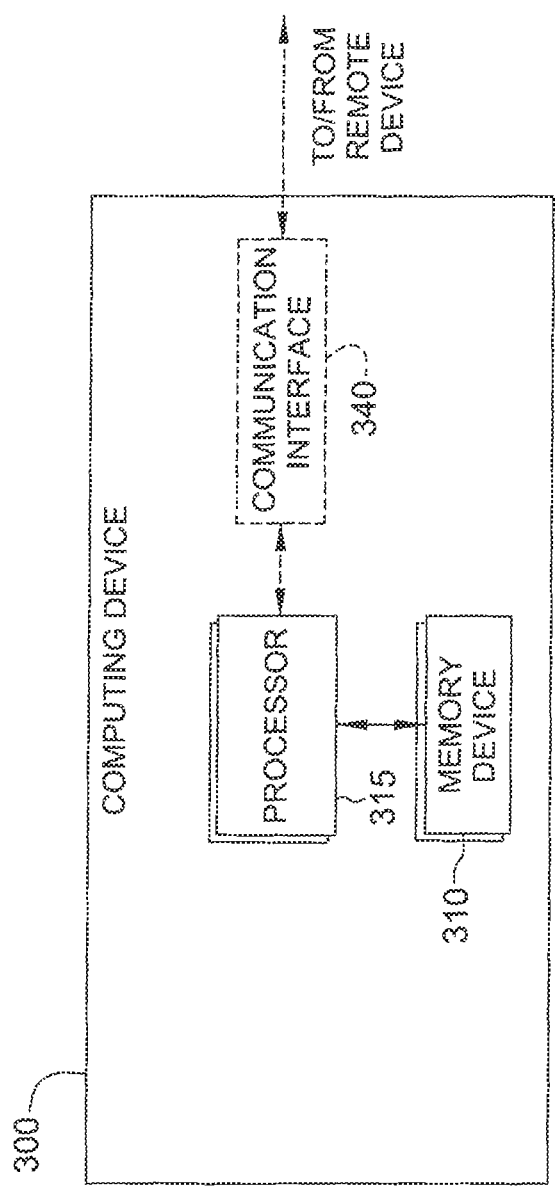
FIG. 3 is a block diagram of one embodiment of a computing device that may be used to control the output architecture shown in FIGS. 2A and 2B.

FIG. 3 is a block diagram of one embodiment of a computing device 300 that may be used to control output architecture 200 (shown in FIGS. 2A and 2B). Computing device 300 may be included, for example, within IPG 150. For example, controller 151 may be implemented using computing device 300.

In this embodiment, computing device 300 includes at least one memory device 310 and a processor 315 that is coupled to memory device 310 for executing instructions. In some embodiments, executable instructions are stored in memory device 310. In the illustrated embodiment, computing device 300 performs one or more operations described herein by programming processor 315. For example, processor 315 may be programmed by encoding an operation as one or more executable instructions and by providing the executable instructions in memory device 310.

Processor 315 may include one or more processing units (e.g., in a multi-core configuration). Further, processor 315 may be implemented using one or more heterogeneous processor systems in which a main processor is present with secondary processors on a single chip. In another illustrative example, processor 315 may be a symmetric multi-processor system containing multiple processors of the same type. Further, processor 315 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 310 is one or more devices that enable information such as executable instructions and/or other data to be stored and retrieved. Memory device 310 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 310 may be configured to store, without limitation, application source code, application object code, source code portions of interest, object code portions of interest, configuration data, execution events and/or any other type of data.

Computing device 300, in the illustrated embodiment, includes a communication interface 340 coupled to processor 315. Communication interface 340 communicates with one or more remote devices, such as a clinician or patient programmer. To communicate with remote devices, communication interface 340 may include, for example, a wired network adapter, a wireless network adapter, a radio-frequency (RF) adapter, and/or a mobile telecommunications adapter.

The embodiments described herein provide systems and methods for an output architecture for an implantable pulse generator. The output architecture includes a power supply, a plurality of outputs, a global source current regulator, a global sink current regulator, a current source branch selector, and a current sink branch selector.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An output architecture for an implantable pulse generator of a neurostimulation system, the output architecture comprising:
   a power supply;
   a plurality of outputs;
   a global source current regulator coupled to the power supply and operable to source a first total current from the power supply to the plurality of outputs through a plurality of source current branches;
   a global sink current regulator operable to sink a second total current from the plurality of outputs to ground through a plurality of sink current branches;
   a current source branch selector operable to select, for each of the plurality of outputs, a fraction of the first total current sourced from the plurality of source current branches, wherein a sum of the fractions of current sourced to each of the plurality of outputs equals the first total current sourced, wherein the current source branch selector comprises a plurality of source selection switches, and wherein each of the plurality of outputs is couplable to each current branch of the plurality of current source branches to source the fraction of the first total current from a particular current source branch of the plurality of current source branches via activation of respective ones of the plurality of source selection switches; and
   a current sink branch selector operable to select, for each of the plurality of outputs, a fraction of the second total current sunk to the plurality of sink current branches, wherein a sum of the fractions of current sunk from each of the plurality of outputs equals the second total current sunk.

2. The output architecture of claim 1, further comprising a plurality of reference voltage switches operable to selectively connect the plurality of outputs to a reference voltage, wherein the plurality of reference voltage switches are distinct from the global source current regulator.

3. The output architecture of claim 1, further comprising a plurality of discharge switches operable to selectively connect the plurality of outputs to at least one discharge rail, and wherein the discharge rail is distinct from the global sink current regulator.

4. The output architecture of claim 1, wherein the global source current regulator comprises a programmable resistor, and an amplifier configured as a voltage digital to analog converter.

5. The output architecture of claim 4, further comprising a second power supply operable to power the amplifier.

6. The output architecture of claim 1, wherein the global sink current regulator comprises a programmable resistor, and an amplifier configured as a voltage digital to analog converter.

7. The output architecture of claim 1, wherein the output architecture is for use in a deep brain simulation system.

8. The output architecture of claim 1, wherein the output architecture is for use in a spinal cord simulation system.

9. The output architecture of claim 1, wherein the current source branch selector comprises a plurality of source decoders, wherein each of the plurality of source decoders is associated with a corresponding source current branch of the plurality of source current branches.

10. The output architecture of claim 1, wherein the current sink branch selector comprises a plurality of sink decoders and a plurality of sink selection switches, wherein each of the plurality of sink decoders is associated with a corresponding sink current branch of the plurality of sink current branches.

11. A neurostimulation system comprising:
   a stimulation lead comprising a plurality of electrodes; and
   an implantable pulse generator communicatively coupled to the stimulation lead, the implantable pulse generator comprising an output architecture that comprises:
   a power supply;
   a plurality of outputs;
   a global source current regulator coupled to the power supply and operable to source a first total current from the power supply to the plurality of outputs through a plurality of source current branches;
   a global sink current regulator operable to sink a second total current from the plurality of outputs to ground through a plurality of sink current branches;
   a current source branch selector operable to select, for each of the plurality of outputs, a fraction of the first total current sourced from the plurality of source current branches, wherein a sum of the fractions of current sourced to each of the plurality of outputs equals the first total current sourced, wherein the current source branch selector comprises a plurality of source selection switches, and wherein each of the plurality of outputs is couplable to each current branch of the plurality of current source branches to source the fraction of the first total current from a particular current source branch of the plurality of current source branches via activation of respective ones of the plurality of source selection switches; and
   a current sink branch selector operable to select, for each of the plurality of outputs, a fraction of the second total current sunk to the plurality of sink current branches, wherein a sum of the fractions of current sunk from each of the plurality of outputs equals the second total current sunk.

12. The neurostimulation system of claim 11, wherein the output architecture further comprises a plurality of reference voltage switches operable to selectively connect the plurality of outputs to a reference voltage.

13. The neurostimulation system of claim 11, wherein the output architecture further comprises a plurality of discharge switches operable to selectively connect the plurality of outputs to at least one discharge rail.

14. The neurostimulation system of claim 11, wherein the global source current regulator comprises a programmable resistor, and an amplifier configured as a voltage digital to analog converter.

15. The neurostimulation system of claim 14, wherein the output architecture further comprises a second power supply operable to power the amplifier.

16. The neurostimulation system of claim 11, wherein the global sink current regulator comprises a programmable resistor, and an amplifier configured as a voltage digital to analog converter.

17. The neurostimulation system of claim 11, wherein the neurostimulation system is a deep brain stimulation system.

18. The neurostimulation system of claim 11, wherein the neurostimulation system is a spinal cord stimulation system.

19. A method of assembling an output architecture for an implantable pulse generator, the method comprising:
   coupling a global source current regulator between a power supply and a plurality of outputs, the global source current regulator operable to source a first total current from the power supply to the plurality of outputs through a plurality of source current branches;
   coupling a global sink current regulator to the plurality of outputs, the global sink current regulator operable to sink a second total current from the plurality of outputs to ground through a plurality of sink current branches;
   coupling a current source branch selector between the global source current regulator and the plurality of outputs, the current source branch selector operable to select, for each of the plurality of outputs, a fraction of the first total current sourced from the plurality of source current branches, wherein a sum of the fractions of current sourced to each of the plurality of outputs equals the first total current sourced, wherein the current source branch selector comprises a plurality of source selection switches, and wherein each of the plurality of outputs is couplable to each current branch of the plurality of current source branches to source the fraction of the first total current from a particular current source branch of the plurality of current source branches via activation of respective ones of the plurality of source selection switches; and
   coupling a current sink branch selector between the global sink current regulator and the plurality of outputs, the current sink branch selector operable to select, for each of the plurality of outputs, a fraction of the second total current sunk to the plurality of sink current branches, wherein a sum of the fractions of current sunk from each of the plurality of outputs equals the second total current sunk.

20. The method of claim 19, further comprising:
   coupling a plurality of reference voltage switches between a reference voltage and the plurality of outputs, the plurality of reference voltage switches operable to selectively connect the plurality of outputs to the reference voltage; and
   coupling a plurality of discharge switches between at least one discharge rail and the plurality of outputs, the plurality of discharge switches operable to selectively connect the plurality of outputs to at least one discharge rail.

* * * * *